US010927391B2

(12) United States Patent
Basheer et al.

(10) Patent No.: US 10,927,391 B2
(45) Date of Patent: Feb. 23, 2021

(54) ENZYMATIC ENRICHMENT OF N-3 FATTY ACIDS IN THE FORM OF GLYCERIDES (71) Applicant: Enzymocore Ltd., Shfaram (IL)

(72) Inventors: Sobhi Basheer, Sakhnine (IL); Ahmad Egbarieh, Musherfeh-Maeleh Eron (IL); Ramez Masri, Nahef (IL)

(73) Assignee: Enzymocore Ltd., Shfaram (IL)

( * ) Notice: Subject to any disclaimer, the term of this patent is extended or adjusted under 35 U.S.C. 154(b) by 0 days.

(21) Appl. No.: 16/070,661

(22) PCT Filed: Dec. 19, 2017

(86) PCT No.: PCT/IL2017/051362
§ 371 (c)(1),
(2) Date: Jul. 17, 2018

(87) PCT Pub. No.: WO2018/116297
PCT Pub. Date: Jun. 28, 2018

(65) Prior Publication Data
US 2019/0048371 A1 Feb. 14, 2019

Related U.S. Application Data (60) Provisional application No. 62/436,078, filed on Dec. 19, 2016.

(51) Int. Cl.
C12P 7/64 (2006.01)
C12N 9/20 (2006.01)
C12N 11/08 (2020.01)

(52) U.S. Cl.
CPC .............. C12P 7/6472 (2013.01); C12N 9/20 (2013.01); C12N 11/08 (2013.01)

(58) Field of Classification Search
CPC .......... C12P 7/6472; C12N 9/20; C12N 11/08
See application file for complete search history.

(56) References Cited

U.S. PATENT DOCUMENTS

| | | | |
|---|---|---|---|
| 4,897,352 A | 1/1990 | Chonde et al. | |
| 5,604,119 A | 2/1997 | Haraldsson et al. | |
| 6,159,523 A | 12/2000 | Cain et al. | |
| 8,765,983 B2* | 7/2014 | Fleischer | C11B 1/106 554/20 |
| 2004/0033571 A1 | 2/2004 | Irimescu et al. | |
| 2005/0233427 A1 | 10/2005 | Schoerken et al. | |
| 2006/0148047 A1 | 7/2006 | Haraldsson et al. | |
| 2014/0017741 A1 | 1/2014 | Nielsen et al. | |
| 2015/0353970 A1 | 12/2015 | Basheer et al. | |

FOREIGN PATENT DOCUMENTS

WO 2015081879 A1 6/2015

OTHER PUBLICATIONS

Hoshino et al., Agric. Biol. Chem., 1990, vol. 54, No. 6, p. 1459-1467.*
Klass & Warvel, Eur. J. Lipid Sci. Technol. 2001, vol. 103, p. 810-814.*
Folch et al., J. Biol. Chem., 1957, vol. 226 p. 497-509.*
Wikipedia "Soxhlet extractor" retrieved on May 1, 2019, 4 pages of PDF.*
Brenneis et al., Biotechnol. Lett, 2012, vol. 34, p. 1459-1463.*
Hernandez et al., Enzyme and Microbial Technology, 2011, vol. 49, p. 72-78.*
Haraldsson et al., JAOCS, 1997, vol. 74, p. 1419-1424.*
Breivik et al., JAOCS, 1997, vol. 74, p. 1425-1429.*
Apr. 12, 2018—(WO) Written Opinion of the International Searching Authority—PCT/IL2017/051362.
International Search Report for PCT/IL2017/051632 dated Apr. 12, 2018.
Watanabe, Yomi, et al., "Stepwise Ethanolysis of Tuna Oil Using Immobilized Candida antarctica Lipase", Journal of Bioscience and Bioengineering, vol. 88, No. 6, (1999), pp. 622-626.
Wang, Yongxin et. al., "MMA/DVB Emulsion Surface Graft Polymerization Initiated by UV Light," Langmuir, vol. 20, (2004), pp. 6225-6231.
Shimada, Yuji, et al., "Enzymatic Purification of Polyunsaturated Fatty Acids," Journal of Bioscience and Bioengineering, vol. 91, No. 6, (2001), pp. 529-538.
Medina, A. Robles, et al., "Lipase-catalyzed esterification of glycerol and polyunsaturated fatty acids from fish and microalgae oils," Journal of Biotechnology, vol. 70, (1999), pp. 379-391.
Jennings, Brenda H., "Enzymatic Modification of Triacylglycerols of High Eicosapentaenoic and Docosahexaenoic Acids Content to Produce Structured Lipids," JAOCS, vol. 76, No. 10, (1999), pp. 1133-1137.
Christensen, Michael Soberg, et al., "Intestinal absorption and lymphatic transport of eicosapentaenoic (EPA), locosahexaenoic (DHA), and decanoic acids: dependence on intramolecular triacylglycerol structure 1-3," Am J Clin Nutr, vol. 61, (1995), pp. 56-61.
Shimada, Yuji, et al., "Ethyl Esterification of Docosahexaenoic Acid in an Organic Solvent-Free System with Immobilized Candida antarctica Lipsase," Journal of Bioscience and Bioengineering, vol. 92, No. 1, (2001), pp. 19-23.
Munio, Maria Del Mar et al., "Synthesis of 2-monoacylglycerols rich in polyunsaturated fatty acids by ethanolysis of fish oil catalyzed by 1,3 specific lipases," Process Biochemistry 43 (2008), pp. 1033-1039.
Bryjak, Jolanta, et al., "Immobilization of lipase on various acrylic copolymers,", Chemical Engineering Journal 65, (1997)), pp. 249-256.
Ortiz, Claudia, et al., "Novozym 435: the "perfect" lipase immobilized biocatalyst?", Royal Society of Chemistry, Catalysis Science & Technology, 2019, 9, pp. 2380-2420.

* cited by examiner

Primary Examiner — Kade Ariani
(74) Attorney, Agent, or Firm — Banner & Witcoff, Ltd.

(57) ABSTRACT

Disclosed are various enzymatic processes for the enrichments of oils with omega-3 fatty acids, and specific lipase preparations for use with these processes.

15 Claims, 2 Drawing Sheets

ENZYMATIC ENRICHMENT OF N-3 FATTY ACIDS IN THE FORM OF GLYCERIDES

TECHNOLOGICAL FIELD

Disclosed are compositions of matter comprising glycerides enriched with n-3 fatty acid moieties, particularly EPA and DHA. Also disclosed are enzymatic methods for preparing the disclosed compositions of matter, which may be one-pot or multi-step multi-enzyme catalyzed reactions, for the production of n-3 polyunsaturated fatty acids-enriched glycerides.

PRIOR ART

References considered to be relevant as background to the presently disclosed subject matter are referred to below. Reference is also made to publications referred to in the above listed publications in their entirety. Acknowledgement of the above references herein is not to be inferred as meaning that these are in any way relevant to the patentability of the presently disclosed subject matter.

BACKGROUND

General

Polyunsaturated fatty acids (PUFA) represent a group of long-chain fatty acids containing two or more double bonds. PUFA are subdivided into two main groups; n-3 (ω-3 or Omega-3) fatty acids and n-6 (ω-3 or Omega-6) fatty acids. The n-3 fatty acids group includes the essential fatty acids α-linolenic acid (ALA, 18:3 n-3) and its long chain metabolites, namely, EPA (eicosapentaenoic acid), DHA (docosahexaenoic acid) and DPA (docosapentaenoic acid), while the n-6 fatty acids group includes, inter alia, arachidonic acid (ARA) and linoleic acid.

Omega-3 fatty acids occur throughout the animal and plant kingdoms. Microorganisms, especially algae, fungi and bacteria are considered as the richest species for this type of fatty acids. These fatty acids are typically present in storage oil triglycerides and also in membrane lipids in the form of fatty acyl groups of esters, phospholipids, ethers, glycolipids, sphingolipids and lipoproteins. Incorporation of PUFA moieties into triglycerides is a most favored form to store these fatty acids, as free fatty acids and short fatty acids alkyl esters, for example fatty acid ethyl esters, are more susceptible to oxidation and degradation. Also, incorporation of fatty acid moieties into triglycerides is favored, because they are readily hydrolyzable to their free form, which is readily absorbed in the digestive system when used in food, nutraceuticals and pharmaceuticals [Christensen, M. S., et al., Am. J. Clin. Nutr. 1995, 61:56].

Enrichment and Separation Methods of n-3 Fatty Acids

Different methods have been applied separately or in combination to concentrate, separate and recover n-3 fatty acids and their derivatives (methyl or ethyl esters, triglycerides and amides) from naturally occurring sources. These methods include primarily fractional crystallization at low temperatures, molecular distillation, urea adduct crystallization, stationary bed chromatography and also the use of lipases. These enrichment methods usually make use of the degree of unsaturation and also the carbon chain-length of fatty acids, which both lead to exhibiting various physical and chemical characteristics with respect to solubility in different solvents, crystallization, melting and evaporation points, polarity and chemical reactivity.

Enrichment of n-3 Fatty Acids by Lipase-Catalyzed Reactions

Lipases are defined as hydrolytic enzymes that act on the ester linkages in triacylglycerol molecules in an aqueous system to yield free fatty acids, partial glycerides and glycerol. In microaqueous organic systems this group of enzymes is capable of catalyzing the reverse hydrolytic reaction [Medina, A. R., et al., J. Biotechnology, 1999, 70:379; Shimada, Y., et al., J. Biosci. Bioeng., 2001, 91(6): 529]. Generally, lipases are classified according to their regiospecificity into two classes, namely random lipases and 1,3-positional specific lipases. In many cases, lipases expose different substrate activities related to the degree of saturation of fatty acids, the chain-length of the fatty acyl group, the position of the double bonds on the carbon chain of the fatty acids, and the geometry of the double bonds on the carbon chain (cis/trans).

Lipase-Catalyzed Hydrolysis of PUFA-Containing Oils

Certain lipases express selectivity to the type of fatty acid residues of triglyceride substrate. For example, lipases derived from *Candida rugosa* and *Candida cylindracea* are enzymes known to possess higher selectivity towards saturated and monounsaturated fatty acid residues in triglycerides. In such a process, after achieving a certain degree of hydrolysis of oil, the organic and aqueous layers are separated. Thereafter, free fatty acids in the organic phase are removed by molecular distillation yielding a concentrate of n-3 fatty acids in the form of glycerides [US Pat. Appl. 2004/0033571 A1]. It is reported that the hydrolysis of tuna fish oil by means of lipase derived from *Candida cylindracea* yielded a glyceride mixture containing 44.1% n-3 fatty acids (18.5% EPA, 17.3% DHA and 3.62% DPA). In order to obtain higher contents of n-3 fatty acids, such as up to 70% of n-3 fatty acids, a second stage of hydrolysis with lipase may be applied on the concentrates obtained in the first stage. It is also reported that multiple hydrolysis stages may decrease recovery yields of the n-3 fatty acids.

Lipase-Catalyzed Selective Esterification of Free Fatty Acids

Some lipases have been identified to have different specificities with regard to the type of fatty acid in esterification reactions of a mixture of various free fatty acids with an alcohol. Such a process is carried out in two stages, hydrolysis of the oil chemically, e.g., with caustic soda, or with random and non-selective lipases in order to obtain free fatty acids and selective-esterification of the free fatty acids obtained in the first stage with a short-chain alcohol using a lipase with preference to certain types of fatty acids [Shimada, Y., et al., (2001) ibid.; U.S. Pat. No. 6,159,523].

This type of two-stage enzymatic process has been used for the enrichment of n-3 fatty acids as well as for the enrichment of individual fatty acids. For example, a free fatty acids hydrolysate obtained by chemical or enzymatic hydrolysis, containing EPA (14%) and DHA (15%) was esterified directly with ethanol, to give EPA and DHA ethyl esters. The reaction is typically catalyzed by a lipase, such as *Mucor miehei* lipase (MML), of high selectivity to saturated, mono- and di-unsaturated fatty acids and to some extent to EPA. The reaction can be stopped, for example, when conversion of the free fatty acid to fatty acid ethyl esters reaches approximately 70%, and the unesterified fatty acids generally contain higher concentrations of DHA. Following this method n-3 fatty acid concentrates containing 49% of DHA and 6% EPA in 73% and 10% recoveries, respectively, were obtained [Watanabe, Y., et al., J. Bioscience and Bioengineering. 1999, 88(6):622; US 2006/0148047 A1].

Lipase-Catalyzed Alcoholysis of PUFA-Containing Oils

Certain lipases possess alcoholysis activity in organic media. In this type of reactions, triglycerides or esters of fatty acids with a medium-chain fatty alcohol, such as n-hexanol, are reacted directly with ethanol or other short-chain alcohol. Lipases of potential use in this type of reactions are those which possess selectivity to a certain type of fatty acids or fatty acyl groups [Watanabe, et al. ibid.; US 2005/0233427, US 2006/0148047; Shimada et al. ibid.]. Two approaches are normally used for enrichment of n-3 fatty acids through alcoholysis reactions:

a. Two-stage alcoholysis reactions where in the first stage a complete alcoholysis of fish oil triglycerides with an alkaline catalyst or with a non-specific lipase to produce ethyl esters of fish oil fatty acids, is carried out. This reaction is typically catalyzed by lipases derived from *Candida antarctica* B. In the second stage, the resulting fish oil fatty acids ethyl esters are transesterified with a longer-chain alcohol, such as n-hexanol, using a lipase with a low selectivity towards n-3 fatty acids, such as *Rhizomucor miehei* lipase to form fatty acids hexyl esters with a low content of n-3 fatty acyl groups and the non-reacted fatty acids ethyl esters with a high content of n-3 fatty acyl groups. The reaction mixture can be treated with fractional distillation in order to obtain a fraction enriched with n-3 fatty acids ethyl esters. The fraction of fatty acid ethyl esters enriched with n-3 fatty acids can be transesterified with glycerol using Novozym 435 (immobilized *Candida antarctica* Lipase B, Novozymes, Denmark) as a catalyst under vacuum and heating up to 65° C. to form triglycerides enriched with n-3 fatty acids.

b. One-stage alcoholysis reaction of fish oil with short-chain alcohols, such ethanol, using lipases possessing low selectivity towards n-3 fatty acid acyl groups to form glycerides enriched with n-3 fatty acids and fatty acid alkyl esters with a low content of n-3 fatty acids as by-products of the transesterification reaction. This process typically produces glycerides with 40-60% n-3 fatty acids, with a recovery yield for n-3 fatty acids typically in the range of 50-70% while the balance of n-3 fatty acids appears in the by-products.

Lipase-Catalyzed Acidolysis Reaction of PUFA-Containing Oils

Research works have described lipase-catalyzed interesterification of plant oils and a rich source of n-3 fatty acids, mostly free fatty acids or their ethyl esters. Lipase derived from *Rhizomucor miehei* (Lipozyme RM IM manufactured by Novozymes) is a common enzyme used in these studies. As this enzyme exhibits 1,3-positional activity, the highest content of PUFA in the final product that could be achieved is 66% [Jennings, B. and Akoh, C. C., J. Am. Oil. Chem. Soc. 1999, 76(10):1133].

Enzymatically prepared pure triglycerides containing individual n-3 fatty acids or their mixtures have also been reported. The process is based on reacting glycerol or partial glycerides containing n-3 fatty acyl groups with pure n-3 fatty acids or their mixtures using Novozym 435® (Novozymes, Denmark). Different preparations of triglycerides containing n-3 fatty acids at contents of higher than 90%, especially for pharmaceutical applications, have been prepared according to this process [U.S. Pat. No. 5,604,119].

SUMMARY

In a first aspect, the present disclosure provides for an enzymatic process for the enrichment of n-3 polyunsaturated fatty acids (n-3 PUFA) as glycerides, said process comprising (a) providing an oil having n-3 PUFA moieties content of from about 5% to about 60% w/w, the n-3 PUFA moieties be present as free acids or as acyl groups of glycerides and/or polar lipids contained in said oil; (b) adding to said oil, water or alkaline aqueous buffer solution at an amount of 0.2-10% w/w of said oil, to give a mixture with pH of from about 5 to about 9; (c) adding to the mixture obtained in step (b) a lipase, wherein said lipase is immobilized on a suitable polymeric support, wherein said lipase exhibits high selectivity toward saturated fatty acids, mono-, di- and tri-unsaturated fatty acids or their fatty acyl groups, and is capable of simultaneously or consecutively transesterifying, hydrolyzing and/or esterifying said oil; (d) providing an alkyl alcohol or alcohol donor, specifically short-chain alkyl alcohol or alcohol donor and adding, specifically step-wise adding said alcohol or alcohol donor to the mixture of said oil and said enzyme preparation obtained in step (c) to form a reaction system comprising said oil, said lipase preparation, said water or aqueous alkaline buffer solution and said alcohol, wherein said oil reacts with said alcohol, and allowing said reaction to reach a conversion of at least 40% of said oil to fatty acid alkyl esters (FAEEs), less than 10% free fatty acid (FFAs) and from about 15% to about 60% glycerides by weight of oil used in the reaction system; (e) stopping the reaction by removing the said reaction medium from said reaction system to give a product comprising FAEEs, FFAs and a mixture of mono-, di- and tri-glycerides, and optionally polar lipids; and (f) isolating the said glycerides from said FAEEs and FFAs by distilling off said fatty acid alkyl esters and free fatty acids from the product obtained in step (f) to give a distillate comprising FAEEs and FFAs, and a residue comprising glycerides mixture and optionally polar lipids, wherein said mixture contains higher omega-3 fatty acids content compared to said oil, with recovery yield of higher than 60%.

The said water or alkaline aqueous buffer solution added at an amount of 0.2-10% w/w of said oil, can be specifically added at an amount of up to 0.2%, 0.5%, 0.75%, 1.0%, 1.5%, 2.0%, 2.5%, 3.0%, 3.5%, 4.0%, 4.5%, 5.0%, 6.0%, 6.5%, 7.5%, 8.0%, 8.5%, 9.0%, 9.5% and up to 10% w/w of said oil.

The pH of the reaction system can be adjusted by the addition of said water or aqueous alkaline buffer solution to about 5.0, 5.5, 6.0, 6.5, 7.0, 7.5, 8.0, 8.5 or 9.0.

In said step (d), the reaction can be allowed to proceed until achieving a conversion of at least 40%, specifically at least 45%, or at least 50% and up to 70% of said oil to fatty acid alkyl esters (FAEEs), less than 10%, specifically 2-8% free fatty acid (FFAs) and from about 15% to about 60%, specifically from about 15%, 20%, 25% to about 30%, 35%, 40%, 45%, 50%, 55% or 60% glycerides by weight of oil used in the reaction system.

The product comprising glycerides mixture and optionally comprising polar lipids obtained in step (f) of the process of said first aspect of the present disclosure, contains higher omega-3 fatty acids content compared to said oil, with recovery yield of higher than 60%, for example higher than 62%, 65%, 68%, 70%, 75% and more.

In specific embodiments of the process of said first aspect, the mixture of fatty acid alkyl esters and free fatty acids distilled off the reaction product in step (f) comprises less than 40% n-3 fatty acid moieties out of the total n-3 fatty acids present in said oil, specifically less than 40%, less than 35%, less than 30%, less than 25%, less than 20%, and even less.

In the said process of said first aspect of the present disclosure, said alcohol can be specifically any one of ethanol or methanol, and said short-alkyl alcohol donor can be any one of dimethyl or diethyl carbonate.

In the said process of said first aspect of the present disclosure, said distillation is any one of molecular distillation, short-path, or thin-film distillation.

In the said process of said first aspect of the present disclosure, said n-3 fatty acid moieties are any one of DHA, DPA and EPA moieties, and any mixture of at least two thereof.

In the said process of said first aspect of the present disclosure, said lipase is derived from any one of *Candida antarctica* A (CALA), *Rhizomucor miehei, Pseudomonas* sp., *Rhizopus niveus, Mucor javanicus, Rhizopus oryzae, Candida antarctica* B (CALB), *Aspergillus niger, Penicillium camembertii, Alcaligenes* sp., *Burkholderia* sp., *Thermomyces lanuginosa* or Chromobacterium *viscosum*, specifically wherein said lipase is derived from *Candida antarctica* A (CALA), *Pseudomonas* sp., *Alcaligenes* sp. or *Thermomyces lanuginose*.

In the said process of said first aspect of the present disclosure, said lipase is immobilized on a hydrophobic porous polymeric resin support, specifically hydrophobic aliphatic or aromatic resin support, particularly hydrophobic aromatic resin is cross-linked divinylbenzene (DVB) or styrene or cross-linked styrene-DVB.

In embodiments of the said process of said first aspect of the present disclosure, the said glycerides mixture obtained in step (f) can be further reacted with at least one of (i) an n-3 FFAs concentrate, or (ii) an n-3 fatty acids short-chain alkyl esters concentrate, in the presence of a suitable lipase, specifically lipase derived from *Candida antarctica* B (CALB), in its free form or immobilized on a polymeric resin support in a reaction mixture under vacuum and a temperature of 30-80° C., to give a glycerides mixture with more than 60%, specifically more about 65%, more than about 70%, and up to about 100% triglycerides containing more than 60% n-3 fatty acids after distillation of the excess of fatty acids ethyl esters and/or fatty acids, and alcohol and/or water byproducts from the reaction mixture.

In the said process of said first aspect of the present disclosure, said oil can be an edible oil, specifically fish or algal oil, fungal oil, or a suitable oleaginous substance containing n-3 fatty acids.

In a second aspect, the present disclosure provides for a method for decreasing the selectivity of lipases towards certain n-3 fatty acids, so that n-3 fatty acids content in the glyceride products of the lipase-catalyzed reactions, including transesterification, esterification and hydrolysis of an oil source is significantly increased, while it is decreased in by-products of the reaction (mainly free fatty acids and fatty acid alkyl esters, when using ethanol fatty acid ethyl esters). Change of selectivity of a lipase, according to the present invention, is achieved by immobilizing the lipase on a specific "mixed" support resin, which has both hydrophobic and hydrophilic domains, as described below, specifically in the description of the third aspect of the invention.

In a third aspect, the present disclosure provides for a method for the immobilization of a lipase on a microporous polymeric resin, the process comprising (a) dissolving said lipase in a suitable buffer solution to give a lipase solution; (b) adding a suitable amount of a microporous polymeric resin to said lipase solution to give a mixture, wherein said microporous polymeric resin comprises alternating domains of hydrophobic monomers and hydrophilic, specifically mild hydrophilic monomers; (c) maintaining the resulting mixture of step (b) at a suitable temperature for a suitable period of time whilst mixing/shaking whereby said lipase is immobilized on said microporous polymeric resin; (d) filtering off the resulting lipase immobilized on said resin to give an immobilized lipase preparation; (e) optionally washing the immobilized lipase preparation with a suitable solvent; and (f) drying the washed immobilized lipase preparation to a level of less than 5% w/w water.

In the said lipase immobilization method, said resin can be a macroreticular porous polymer having alternating hydrophobic domains and hydrophilic domains, specifically hydrophobic domains comprised of hydrophobic aliphatic or aromatic monomers and mild hydrophilic domains comprised of acrylic, or methacrylic esters, such as divinylbenzene-cross-linked with methyl methacrylate.

In the said lipase immobilization method, the weight ratio between said hydrophobic domains and between said mild hydrophilic domains is from about 10:0.1 to about 1:10, respectively, more specifically from 10-99% to 90-1%, respectively.

In the said lipase immobilization method, said macroreticular porous polymer having alternating hydrophobic domains and hydrophilic domains can be divinylbenzene cross linked with methyl methacrylate, wherein the ratio of divinylbenzene domains to methylmethacrylate domains is from 10-99 to 90-1, respectively.

In the said lipase immobilization method, said lipase can be a lipase having high selectivity toward transesterification/esterification/hydrolysis of saturated fatty acids, mono-, di- and tri-unsaturated fatty acids, as free fatty acids or in the form of fatty acyl groups, and low selectivity toward the transesterification/esterification/hydrolysis of n-3 fatty acids as free fatty acids or as fatty acyl groups. Specifically, said lipase can be a lipase derived from any one of *Candida antarctica* A (CALA), *Rhizomucor miehei, Pseudomonas* sp., *Rhizopus niveus, Mucor javanicus, Rhizopus oryzae, Aspergillus niger, Penicillium camembertii, Alcaligenes* sp., *Candida antarctica* B (CALB), *Burkholderia* sp., *Thermomyces lanuginosa* or Chromobacterium *viscosum*.

In the said lipase immobilization method, said suitable temperature can be from 10 to 50° C., said suitable time can be from about 0.5 to 48 hours, specifically about 6 hours, said solvent suitable for washing the immobilized lipase preparation can be acetone or water, and said drying can be conducted in a desiccator or lyophilizer.

In the said lipase immobilization method, the resulting immobilized lipase preparation can be dried to a water content of less than 5% w/w, specifically less than 2% w/w, more specifically less than 1.5% w/w, particularly less than 1% w/w.

In the said lipase immobilization method, the selectivity of said lipase toward n-3 fatty acids, which can be in free form or in esterified form as in glycerides or alkyl esters, in any of transesterification, interesterification, esterification or hydrolysis reactions is modulated, specifically said activity is decreased while maintaining the catalytic activity of said lipase. The n-3 fatty acids can be present in free form or as fatty acid moieties of mono-, di- or triglycerides, or polar lipids of an oil, specifically an edible oil, more specifically fish oil, fungal oil or an edible oleaginous substance containing n-3 fatty acids.

The lipase prepared by the said immobilization method can retain at least 70% of its catalytic activity over at least 10 reaction cycles, using the same batch of immobilized enzyme.

In a fourth aspect, the present disclosure provides for an immobilized lipase preparation comprising a lipase immobilized on a microporous polymeric resin support, wherein said macroreticular porous polymeric resin comprises mixed hydrophobic domains and mild hydrophilic domains, wherein said hydrophobic domains are comprised of a hydrophobic aliphatic or aromatic monomers and said hydrophilic domains are comprised of a mild hydrophilic monomers, specifically acrylic or methacrylic esters, or any combination thereof.

In the immobilized lipase preparation according to the present disclosure, said macroreticular porous polymer having alternating hydrophobic domains and hydrophilic domains can be divinylbenzene cross linked with methyl methacrylate, wherein the ratio of divinylbenzene domains to methylmethacrylate domains is from 10-99% to 90-1%, for example, but not limited to 10-98% to 90-2%, respectively.

The immobilized lipase preparation according to the present disclosure can exhibit lipase has high selectivity toward transesterification/esterification/hydrolysis of saturated fatty acids, mono-, di- and tri-unsaturated fatty acids, as free fatty acids or in the form of fatty acyl groups, and low selectivity toward the transesterification/esterification/hydrolysis of n-3 fatty acids as free fatty acids or as fatty acyl groups.

The immobilized lipase preparation according to the present disclosure can be a lipase derived from any one of *Candida antarctica* A (CALA), *Rhizomucor miehei*, *Candida antarctica* B (CALB), *Pseudomonas* sp., *Rhizopus niveus*, *Mucor javanicus*, *Rhizopus oryzae*, *Aspergillus niger*, *Penicillium camembertii*, *Alcaligenes* sp., *Burkholderia* sp., *Thermomyces lanuginosa* or Chromobacterium viscosum.

The immobilized lipase preparation according to the present disclosure can retain at least 70% of its catalytic activity over at least 10 reaction cycles.

In a fifth aspect, the present disclosure provides for process for the preparation of a mixture of glycerides having from about 30% to about 80% w/w, specifically from about 50% to 80% w/w, more specifically from about 50% to 70% w/w, more specifically from about 30%, 35%, 40%, 45%, or 50% to about 70%, 72%, 75%, 78% or 80% n-3 polyunsaturated fatty acids moieties, said process comprising (a) providing an oil comprising n-3 polyunsaturated fatty acids, specifically from about 5% to about 60% w/w, said n-3 fatty acids being present as fatty acyl groups bonded to the glycerol backbone of glycerides and/or of polar lipids in said oil and/or as free fatty acids, said oil also comprising free or esterified saturated fatty acids, mono-, di- and tri-unsaturated fatty acids; (b) adding to said oil, water or alkaline aqueous buffer solution at an amount of 0.2-10% w/w of said oil, to give a mixture with pH of from about 5 to about 9; (c) adding to the mixture obtained in step (b) a lipase, wherein said lipase is immobilized on a polymeric resin support, wherein said resin comprises alternating hydrophobic domains and mild hydrophilic domains, specifically hydrophobic domains comprised of hydrophobic aliphatic or aromatic monomers and mild hydrophilic domains comprised of acrylic and/or methacrylic esters, wherein said lipase exhibits high selectivity towards saturated fatty acids, mono-, di- and tri-unsaturated fatty acids or their fatty acyl groups, and is capable of simultaneously or consecutively transesterifying, hydrolyzing and/or esterifying said oil; (d) providing an alkyl alcohol or alcohol donor, specifically short-chain alkyl alcohol or alcohol donor and adding, specifically step-wise adding said alcohol or alcohol donor to the mixture of said oil and said enzyme preparation obtained in step (c) to form a reaction system comprising said oil, said lipase preparation and said alcohol, wherein said oil reacts with said alcohol, and allowing said reaction to reach a conversion of at least 40% of said oil to fatty acid alkyl esters (FAEEs), less than 10% free fatty acid (FFAs) and from about 15% to about 60% glycerides by weight of oil used in the reaction system; (e) stopping the reaction by removing the said reaction medium from said reaction system to give a product comprising FAEEs, FFAs and a mixture of mono-, di- and tri-glycerides and optionally polar lipids; and (f) isolating the said glycerides mixture from said FAEEs and FFAs by distilling off said fatty acid alkyl esters and free fatty acids from the product obtained in step (f) to give a distillate comprising FAEEs and FFAs, and a residue comprising glycerides mixture, wherein said glycerides mixture optionally further comprises polar lipids contains higher omega-3 fatty acids content compared to said oil, with recovery yield for omega-3 fatty acids of higher than 60%.

In the process of said fifth aspect of the present disclosure, the said water or alkaline aqueous buffer solution can be added at an amount of 0.2-10% w/w of said oil, can be specifically added at an amount of up to 0.2%, 0.5%, 0.75%, 1.0%, 1.5%, 2.0%, 2.5%, 3.0%, 3.5%, 4.0%, 4.5%, 5.0%, 6.0%, 6.5%, 7.5%, 8.0%, 8.5%, 9.0%, 9.5% and up to 10% w/w of said oil, and the pH of the reaction system can be adjusted by the addition of said water or alkaline aqueous buffer solution to about 5.0, 5.5, 6.0, 6.5, 7.0, 7.5, 8.0, 8.5 or 9.0.

In said step (d) of the process of said fifth aspect of the present disclosure, the reaction can be allowed to proceed until achieving a conversion of at least 40%, specifically at least 45%, or at least 50% and up to 70% of said oil to fatty acid alkyl esters (FAEEs), less than 10%, specifically 2-8% free fatty acid (FFAs) and from about 15% to about 60%, specifically from about 15%, 20%, 25% to about 30%, 35%, 40%, 45%, 50%, 55% or 60% glycerides by weight of oil used in the reaction system.

In said process of said fifth aspect of the present disclosure, the product comprising glycerides mixture and optionally comprising polar lipids obtained in step (f), contains higher omega-3 fatty acids content compared to said oil, with recovery yield of higher than 60%, for example higher than 62%, 65%, 68%, 70%, 75% and more.

In said process of said fifth aspect of the present disclosure, the mixture of fatty acid alkyl esters and free fatty acids distilled off the reaction product in step (f) comprises less than 40% n-3 fatty acid moieties out of the total n-3 fatty acids present in said oil, specifically less than 40%, less than 35%, less than 30%, less than 25%, less than 20%, and even less.

In the said process of said fifth aspect of the present disclosure, said oil can be an edible oil, specifically fish or algal oil, fungal oil, or a suitable oleaginous substance containing n-3 fatty acids.

In the said process of said fifth aspect of the present disclosure, said alcohol can be specifically any one of ethanol or methanol, and said short-alkyl alcohol donor can be any one of dimethyl or diethyl carbonate.

In the said process of said fifth aspect of the present disclosure, said distillation is any one of molecular distillation, short-path, or thin-film distillation.

In the said process of said fifth aspect of the present disclosure, said n-3 fatty acid moieties are any one of DHA, DPA and EPA moieties, and any mixture of at least two thereof.

In the said process of said fifth aspect of the present disclosure, said lipase is derived from any one of *Candida antarctica* A (CALA), *Rhizomucor miehei*, *Pseudomonas* sp., *Rhizopus niveus, Mucor javanicus, Rhizopus oryzae, Candida antarctica* B (CALB), *Aspergillus niger, Penicillium camembertii, Alcaligenes* sp., *Burkholderia* sp., *Thermomyces lanuginosa* or *Chromobacterium viscosum*, specifically wherein said lipase is derived from *Candida antarctica* A (CALA), *Pseudomonas* sp., *Alcaligenes* sp. or *Thermomyces lanuginose*.

In the said process of said fifth aspect of the present disclosure, said hydrophobic aromatic monomers are divinylbenzene (DVB) and/or styrene and wherein optionally said mild hydrophilic monomers are acrylic or methacrylic esters, or combined acrylic/methacrylic esters. The weight ratio between said hydrophobic monomers and said mild hydrophilic monomers can be from about 10:0.1 to about 1:10, respectively, more specifically 10-99% to 90-1%, respectively.

In embodiments of the said process of said fifth aspect of the present disclosure, the said glycerides mixture obtained in step (f) can be further reacted with at least one of (i) an n-3 FFAs concentrate, or (ii) an n-3 fatty acids short-chain alkyl esters concentrate, in the presence of a suitable lipase, specifically lipase derived from *Candida antarctica* B (CALB), in its free form or immobilized on a polymeric resin support in a reaction mixture under vacuum and a temperature of 30-80° C., to give a glycerides mixture with more than 60%, specifically more than about 65%, more than about 70%, and up to about 100% triglycerides containing more than 60% n-3 fatty acids after distillation of the excess of fatty acids ethyl esters and/or fatty acids, and alcohol and/or water byproducts from the reaction mixture.

In a sixth aspect, the present disclosure provides for a process for enzymatic preparation of n-3 fatty acid short-chain alkyl esters, specifically n-3 fatty acid ethyl esters, the process comprising: (a) providing an oil comprising n-3 polyunsaturated fatty acids, specifically from about 5% to about 60% w/w, said n-3 fatty acids being present as fatty acyl groups bonded to the glycerol backbone of glycerides and optionally polar lipids in said oil and/or as free fatty acids, said oil also comprising free or esterified saturated fatty acids, mono-, di- and tri-unsaturated fatty acids; (b) adding to said oil, water or alkaline aqueous buffer solution at an amount of 0.2-10% w/w of said oil, to give a mixture with pH of from about 5 to about 9; (c) adding to the mixture obtained in step (b) a *Pseudomonas* sp. lipase (PS lipase) preparation in which said PS lipase immobilized on a polymeric resin support at a high load, specifically higher than 10,000 units of said PS lipase per 1 g of polymer support, wherein said resin comprises alternating hydrophobic domains and mild hydrophilic domains, specifically hydrophobic domains comprised of hydrophobic aliphatic or aromatic monomers and mild hydrophilic domains comprised of acrylic and/or methacrylic esters, wherein said PS lipase exhibits high selectivity towards saturated, mono-, di- and tri-unsaturated fatty acids in their free form or when bound to glycerol or to polar lipids, and is capable of simultaneously or consecutively transesterifying/esterifying/hydrolyzing said fatty acids; (d) providing a short-chain alkyl alcohol, specifically ethanol, and adding, specifically step-wise adding, said alcohol to the mixture of said oil and said enzyme preparation obtained in step (c), to form a reaction system comprising said oil, said lipase preparation, said water or aqueous buffer solution and said alcohol, wherein said oil reacts with said alcohol, and allowing said reaction to reach a conversion of about 70% of said oil to fatty acid alkyl esters and less than 10% FFAs; (e) stopping the reaction by removing the said first lipase preparation and collecting the organic upper phase/fraction of the reaction mixture containing fatty acids alkyl esters (FAEEs), mono-, di- and the residual tri-glycerides, in addition to free fatty acids byproducts and excess of alcohol; (f) reacting the said organic phase obtained in step (e) with a short-chain alkyl alcohol, specifically ethanol, in the presence of *Thermomyces lanuginosa* lipase (TL) immobilized on a polymeric resin support, wherein said resin comprises alternating hydrophobic domains and mild hydrophilic domains, specifically hydrophobic domains comprised of hydrophobic aliphatic or aromatic monomers and mild hydrophilic domains comprised of acrylic and/or methacrylic esters, and allowing the reaction to continue until at least 97% conversion, specifically 98%, 99% and up to 100% of fatty acyl groups in said oil are converted to their lower alkyl esters, specifically ethyl esters; (g) stopping the reaction by removing the said lipase preparation from the reaction mixture; and (h) isolating said n-3 polyunsaturated fatty acid alkyl esters concentrate from the reaction mixture by fractional distillation.

In the process of said sixth aspect of the present disclosure, said resin support for both said PS lipase and said TL lipase comprises alternating hydrophobic domains comprised of cross-linked divinylbenzene monomers, cross-linked styrene monomer or crosslinked styrene and divinylbenzene monomers and said mild hydrophilic domains comprised of acrylic and/or methacrylic esters.

In the process of said sixth aspect of the present disclosure, said PS lipase can be immobilized on said polymeric resin support at a load of from about 5,000 to about 50,000 units per 1 gram of said support, specifically from about 15,000 to 30,000 units per 1 gram of said support, more specifically from about 20,000 to 25,000 per 1 gram of said support.

In the process of said sixth aspect of the present disclosure, the weight ratio between said hydrophobic resin domains and said mild hydrophilic domains can be from about 10:0.1 to about 1:10, respectively. More specifically, the weight ratio between said hydrophobic resin domains and said mild hydrophilic domains can be 10-99% to 90-1%, respectively.

In the process of said sixth aspect of the present disclosure, said PS lipase preparation and said TL lipase preparation maintain at least 70% of their catalytic activity over at least 20 reaction cycles using the same batch of each said PS lipase preparation and TL lipase preparation.

In the process of said sixth aspect of the present disclosure, said organic upper phase/fraction can be collected by any one of gravity separation, centrifugation or passing the reaction mixture through a column packed with a glycerol/water-adsorbing resin.

In embodiments of the process of said sixth aspect of the present disclosure, the isolated 3-n polyunsaturated fatty acid alkyl esters concentrate obtained in step (h), specifically ethyl esters, can be further reacted with glycerol, in the presence of a lipase capable of transesterifying the n-3 fatty acyl moieties of said alkyl esters concentrate to said glycerol, specifically a lipase derived from *Candida antarctica* B (CALB), wherein said lipase is optionally immobilized on a suitable polymeric resin support, wherein the reaction system comprises water at up to about 1% per weight of said isolated 3-n polyunsaturated fatty acid alkyl esters concentrate, and allowing the reaction to proceed until a mixture of glycerides comprising more than 50% triglycerides of the total formed glycerides is formed after removal of unreacted glycerol and distillation of excess of fatty acids/fatty acid alkyl esters, and alkyl alcohol, specifically ethanol and/or water as by-products.

In the process of said sixth aspect of the present disclosure, the polymeric resin support on which said lipase is immobilized can comprise alternating hydrophobic domains and mild hydrophilic domains, specifically hydrophobic domains comprised of hydrophobic aliphatic or aromatic monomers, specifically divinylbenzene and/or styrene, and mild hydrophilic domains comprised of acrylic and/or methacrylic esters.

In the process of said sixth aspect of the present disclosure, the n-3 fatty acid moieties in said oil can be any one of DHA, DPA and EPA moieties, and any mixture of at least two thereof. The said n-3 fatty acids can be present in free form or as fatty acid moieties of mono-, di- or triglycerides, or polar lipids of an oil, specifically fish and oleaginous oils.

BRIEF DESCRIPTION OF THE DRAWINGS

In order to better understand the subject matter disclosed herein and to exemplify how it can be carried out in practice, embodiments will now be described, by way of non-limiting example only, with reference to the accompanying drawings, in which.

DETAILED DESCRIPTION

Provided herein are new methods and processes for enriching oils with polyunsaturated fatty acids (PUFAs), particularly n-3 polyunsaturated fatty acids (n-3 PUFA or n-3 fatty acids, used herein interchangingly), in particular DHA, DPA and EPA.

Further provided herein are compositions of glycerides enriched with n-3 polyunsaturated fatty acids, and n-3 polyunsaturated fatty acids concentrates, the main constituents of which are tri-, di- or mono-glycerides and any mixture of at least two thereof, with high levels of n-3 polyunsaturated fatty acyl moieties attached to the glycerol backbone.

The presently disclosed processes use various lipase preparations, comprising lipase/s in immobilized forms, for the enrichment of oils, specifically but not limited to fish oil, with n-3 polyunsaturated fatty acids in the form of triglycerides or partial glycerides, described below in detail. The presently disclosed processes offer an alternative compared to the conventional processes described above.

Provided herein are processes and methods employing various different combinations of lipase-catalyzed reactions and molecular distillation, for enrichment of oils with n-3 polyunsaturated fatty acids, particularly for obtaining n-3 polyunsaturated fatty acids concentrates in the form of glycerides, in which more than 40% w/w out of the total fatty acid moieties of the glycerides are n-3 fatty acid moieties, with improved recovery rate, typically more than 60% w/w of the initial content of n-3 fatty acids in the starting materials.

In a first aspect, the present disclosure provides for a reaction between oil as source of n-3 fatty acids and a short-chain alcohol or alcohol source using immobilized lipase preparations comprising a lipase or mixture of lipases with substrate specificity and selectivity, as disclosed herein, allows for the production of glycerides of high content of n-3 polyunsaturated fatty acids and reduced content of n-3 polyunsaturated fatty acids in the fatty acids alkyl esters and free fatty acids by-products of the reaction, thereby enriching the oil source with n-3 PUFA.

In a second aspect, the present disclosure also provides for a method for decreasing the selectivity of lipases towards certain n-3 fatty acids, so that n-3 fatty acids content in the glyceride products of the lipase-catalyzed reactions, including transesterification, esterification and hydrolysis of an oil source is significantly increased, while it is decreased in by-products of the reaction (mainly free fatty acids and fatty acid alkyl esters, when using ethanol fatty acid ethyl esters). Change of selectivity of a lipase, according to the present invention, is achieved by immobilizing the lipase on a specific "mixed" support resin, which has both hydrophobic and hydrophilic domains, as described below.

Thus, in a third aspect, the present disclosure provides for a method for immobilization of lipases on a microporous polymeric resin that comprises both hydrophobic domains, comprised of hydrophobic polymer (throughout this description any number of linked monomers) and mild hydrophilic domains (throughout this description any number of linked monomers), comprising of a hydrophilic polymer. By the term "mild" as used herein, is meant a hydrophilic polymeric stretch or segment comprising monomers with an ester group, which on the formed mixed resin cannot produce hydrogen bonding between neighboring polymeric chains. Lipases immobilized on such "mixed" hydrophobic-hydrophilic resins as provided herein, can lead to increased transesterification/esterification activity towards saturated fatty acids and, to some extent, towards certain mono-, di- and tri-unsaturated fatty acids in the form of free fatty acids or in the form of fatty acyl groups of glycerides, and low selectivity towards the transesterification/esterification of n-3 fatty acids in the form of free fatty acids or fatty acyl groups. The "domains" of this polymeric resin support are also referred to herein as "segments" or "stretches", i.e. stretches/segments of a hydrophobic polymer, essentially alternating with stretches/segments of a mild hydrophilic polymer. The polymeric supports provided herein comprise alternating hydrophilic domains and hydrophobic domains (and may also be referred to as "mixed supports" or "mixed resins"). For example, the "mixed" polymeric support can be a support having alternating domains comprised of hydrophobic aliphatic or aromatic domains and domains comprised of mild hydrophilic domains, such as acrylic or methacrylic esters domains, or any mix of thereof. The mild hydrophilic domains can be of different or identical length (different number of monomers), and so may the hydrophobic domains be of different or identical length (different number of monomers). In the present disclosure the use of macroreticular porous polymeric supports comprising divinylbenzene-cross-linked with acrylic or methacrylic esters is presented as a non-limiting example of a mixed support. As mentioned above, it is to be understood that when referring to "a domain comprised of mild hydrophilic polymer" or "domain comprised of hydrophobic polymer", is meant any length/number of linked, specifically cross linked, mild hydrophilic monomers, or hydrophobic monomers, where the stretches need not be of conventional "polymer" length, and can comprises from one and/or few monomers, such as in oligomers, to numerous monomers, such as in polymers.

In a fourth aspect, provided herein are lipase preparations, in which the lipase is immobilized on a microporous polymeric resin support, the resin having hydrophobic domains and mild hydrophilic domains, as described above. This polymeric support comprises alternating mild hydrophilic domains and hydrophobic domains (and may also be referred to as "mixed supports" or "mixed resins").

In said third and fourth aspects of the present disclosure, and throughout, the mixed polymeric support can be a polymeric resin having alternating domains of hydrophobic aliphatic or aromatic linked monomers and domains of mild hydrophilic acrylic or methacrylic esters linked monomers. The mild hydrophilic domains in the mixed resin can be of different or identical length (different number of monomers), and so can the hydrophobic domains in the mixed resin be of different or identical length (different number of monomers). In a specific embodiment of the method of immobilizing a lipase on a mixed support and a specific embodiment of the lipase immobilized on a mixed support, the lipase-immobilizing support is a macroreticular porous polymeric support comprising alternating domains of divinylbenzene (DVB) (or mixture of divinylbenzene and styrene at different ratios) cross-linked with acrylic or methacrylic esters (MMA). The disclosed lipase preparations immobilized on a mixed support exhibit increased transesterification/esterification activity towards saturated fatty acids and, to some extent, towards mono-, di- and tri-unsaturated fatty acids in the form of free fatty acids or in the form of fatty acyl groups, and low selectivity towards the transesterification/esterification of n-3 fatty acids in the form of free fatty acids or fatty acyl groups, compared to free lipases or lipases immobilized on other supports, such as hydrophilic or hydrophobic supports.

The terms "polymeric support", "polymeric matrix", "immobilizing support", "polymeric substrate", "resin support", "resin matrix", "immobilizing resin", "resin substrate", "polymeric carrier" and the like are used herein interchangingly, and refer to solid or semi-solid polymeric/resinous bodies on which an enzyme, specifically a lipase can be chemically or physically immobilized.

The terms "polymeric domains" or "polymeric segments" or "polymeric fragments" or "polymeric stretches" and the like, used herein as components of polymeric supports for immobilization of enzymes, specifically lipases, are to be taken to mean parts of such polymeric supports.

In a fifth aspect, the present disclosure provides for a method for the enzymatic enrichment oils with n-3 PUFA, essentially comprising a reaction between oil as source of n-3 fatty acids and a short-chain alcohol or alcohol donor, using a lipase immobilized on the disclosed "mixed" hydrophobic-hydrophilic support (resin), that results of glycerides of high content of n-3 fatty acids compared to the starting oil source, and reduced content of n-3 fatty acids in the fatty acids alkyl esters and free fatty acids by-products of the enzymatic reaction.

For example, according to this aspect, the process for enrichment of oil that contains from 5% to 60% w/w, specifically from 10% to 30% w/w or more polyunsaturated fatty acids, in particular DHA, DPA and EPA, comprises the steps of:

(a) transesterifying/esterifying and hydrolysis, simultaneously or consecutively, an oil containing n-3 fatty acids with an alcohol or alcohol donor, using a lipase of high selectivity towards in particular saturated, and to some extent mono-, di- and tri-unsaturated fatty acids or their acyl moiety, immobilized on a polymeric resin having hydrophobic-hydrophilic domains; and (b) removing the immobilized lipase preparation and isolating the formed glycerides, containing higher than 50% w/w n-3 fatty acids of the total n-3 fatty acids in the starting material, from the formed fatty acid alkyl esters and free fatty acids, which containing less than 50% n-3 fatty acids of the total n-3 fatty acids in the starting material, to give a glycerides fraction enriched with n-3 fatty acids.

It is noted that in all aspects of the present disclosure, the said transesterification can be a one-step direct transesterification, or it can be achieved through a hydrolysis reaction followed by consecutive esterification of formed free fatty acids with an alcohol. Esterification can also be that of any free fatty acids present in the reaction medium with the short-chain alcohol.

In a sixth aspect, the present disclosure provided an all-enzymatic two-steps process for the preparation of fatty acid alkyl esters, specifically fatty acids ethyl esters, as described in detail above and in the examples below. Generally, this process provides for enzymatic preparation of n-3 fatty acid short-chain alkyl esters, specifically n-3 fatty acid ethyl esters, in which an oil comprising n-3 polyunsaturated fatty acids, is reacted with a short-chain alkyl alcohol, specifically ethanol, in the presence of water or alkaline aqueous buffer solution, at pH of about 5-9, and in the presence of *Pseudomonas* sp. lipase (PS lipase) preparation in which said PS lipase immobilized on a polymeric resin support at a high load, specifically higher than 10,000 units of said PS lipase per 1 g of polymer support, wherein said support is a mixed polymeric support in accordance with the present disclosure. The reaction is allowed to proceed until conversion of about 70% of said oil to fatty acid alkyl esters and less than 10% FFAs is achieved, and is then stopped by removing the said PS lipase preparation and collecting the organic upper phase/fraction of the reaction mixture containing fatty acids alkyl esters (FAEEs), mono-, di- and the residual tri-glycerides, in addition to free fatty acids byproducts and excess of alcohol. In a second step, the said organic phase is reacted with a short-chain alkyl alcohol, specifically ethanol, in the presence of *Thermomyces lanuginosa* lipase (TL) immobilized on a mixed polymeric resin support in accordance with the present disclosure, and the reaction is allowed to continue until at least 97% w/w, specifically 98% w/w, 99% w/w and up to 100% of fatty acyl groups in said oil are converted to their lower alkyl esters, specifically ethyl esters. The reaction is then stopped by removing the said lipase preparation from the reaction mixture, and the obtained n-3 polyunsaturated fatty acid alkyl esters concentrate are isolated from the reaction mixture by fractional distillation. As shown in Example 6 below, in this process, the PS lipase preparation and the TL lipase preparation both maintained at least 70% of their catalytic activity over at least 20 reaction cycles using the same batch of each said PS lipase preparation and TL lipase preparation.

In embodiments of all aspects of the disclosed processes/reactions, the glycerides fraction enriched with n-3 PUFAs can be isolated from the reaction mixture by treating the reaction mixture with molecular/thin film distillation, to remove the fraction rich with fatty acid alkyl esters and free fatty acids, whereby following distillation, the n-3 PUFAs enriched glyceride fraction comprises a mixture of mono-, di- and tri-glycerides with at least 60% w/w recovery yield for n-3 PUFAs.

In embodiments all aspects of the disclosed processes/reactions, the resulting isolated enriched glycerides fraction can optionally be further enzymatically reacted with n-3 PUFAs concentrate (of mainly free fatty acids), or n-3 PUFA short-chain alkyl esters, in the presence of, for example, *Candida antarctica* lipase B or with other enzyme preparation of similar activity of catalyzing esterification of fatty acids with no preference to degree of unsaturation or length of carbon chain in free fatty acids or in fatty acyl groups. The enzyme can be used in its free form or immobilized on a polymeric resin, to obtain a mixture comprising mainly triglycerides further enriched with n-3 fatty acids, typically, more than 60% w/w, and water or alcohol as by-products of the reaction, respectively. Following removal of the enzyme from the reaction mixture and subsequent distillation of water and/or alcohol and any unreacted fatty acids or fatty acid alkyl esters, respectively, a mixture, comprising mainly triglycerides, containing more than 60% w/w n-3 fatty acid moieties is obtained.

Certain lipases can give recovery yields of n-3 fatty acid moieties in the glycerides fraction, for example of less than 70% w/w of the initial n-3 fatty acids content of the oil used, with the balance of the n-3 fatty acid moieties transesterified into the byproduct fatty acids alkyl esters mixture and in the hydrolysis byproduct, namely free fatty acids mixture. When such lipases are used, in embodiments of all aspects of the disclosed processes/reactions, the reaction mixture can be further treated with the following steps:
a. Removal of the enzyme from the reaction mixture, followed with evaporation, specifically flash evaporation, in order to remove alcohol and water byproducts from the reaction mixture;
b. Optionally, treatment of the resulting reaction mixture with a second lipase, in its free or immobilized form, in order to catalyze one-pot selective esterification, transesterification and interesterification between the reaction components (glycerides) and concentrates of fatty acid alkyl esters or free fatty acids to produce glycerides of higher content of n-3 fatty acid in the form of triglycerides;
c. Removal of the enzyme and treatment of the reaction mixture with molecular/thin film distillation in order to remove excess of fatty acid alkyl esters and free fatty acids, to give a residue comprising of glycerides mixture, mainly triglycerides, with n-3 fatty acid moieties contents higher than 60%.

In all aspects and embodiments of the present disclosure, the oil used in the various reactions and processes can be an edible oil, e.g., fish or algal oil, fungal oil, or any other suitable oleaginous substances containing n-3 fatty acids.

In all aspects and embodiments of the present disclosure, the alcohol can be an alkyl alcohol, for example but not limited to short chain alkyl alcohol. By "short chain alkyl alcohol" as used herein is meant $C_1$-$C_6$-alkyl alcohol, specifically $C_1$-$C_4$-alkyl alcohol, such as methanol and ethanol. By "short-chain alcohol donor" as used herein is meant a mono-short-chain alkyl ester, e.g. methyl acetate or ethyl acetate, or a di-short-chain-alkyl carbonate, e.g. dimethyl- or diethyl carbonate.

The lipase used in the various reactions and processes disclosed herein, or their different stages, where present, can be derived from, e.g., any of *Candida antarctica* A, *Candida antarctica* B (CALB), *Rhizomucor miehei, Candida rugosa, Candida cylindracea, Pseudomonas* sp., *Rhizopus niveus, Mucor javanicus, Rhizopus oryzae, Aspergillus niger, Aspergillus oryzae, Penicillium camembertii, Alcaligenes* sp., *Burkholderia* sp., *Humicola insolens, Thermomyces lanuginosa* or Chromobacterium *viscosum*. The use of mixtures of enzymes is contemplated.

The terms "enzyme selectivity", "enzyme specificity" and "enzyme preference" are used herein interchangingly.

In all aspects and embodiments of the present disclosure, the lipase used in the described reactions and processes can be free, or it can be immobilized on a microporous polymeric resin. For example, particularly in said first aspect of the present disclosure, the microporous polymeric resin can be a hydrophobic microporous organic polymeric resin comprising aliphatic or aromatic groups, for example cross linked divinylbenzene or cross-linked styrene and divinylbenzene. In some specific aspects and embodiments, for example said second, third, fourth, fifth or sixth aspects of the present disclosure, the lipase is immobilized on a "mixed" microporous polymeric resin which generally has alternating hydrophobic-hydrophilic domains, as herein disclosed. Macroreticular porous polymeric supports made of divinylbenzene-cross-linked with methacrylic esters are one example of a mixed support that can be used in the embodiments of the processes disclosed herein. These polymeric supports are characterized by their alternating hydrophobic and mild hydrophilic domains, such as hydrophobic domains of linked aliphatic or aromatic monomers and hydrophilic domains of linked hydrophilic acrylic or methacrylic esters monomers. When referring to "linked", it specifically designates "cross-linked". Mild hydrophilic monomers include acrylic alkyl esters and methacrylic alkyl esters, while hydrophobic monomers include divinylbenzene, styrene, and propylene. Specific combinations disclosed and exemplified herein are polymers comprising different ratios of divinylbenzene and methyl methacrylate monomers, in alternating stretches.

As presented in the experimental section of the present disclosure, the recovery yield of the n-3 fatty acids in the form of fatty acids moieties in the glyceride product, using lipase/s immobilized on a "mixed" support as disclosed herein, is significantly increased. Further, when a lipase is immobilized on the disclosed mixed support, it exhibits unique catalytic properties with regard to preference towards the various types of fatty acids, saturated, unsaturated, or polyunsaturated fatty acids, in free form or as fatty acyl moieties (e.g. fatty acid alkyl esters and mono-, di- and tri-glycerides and polar lipids). Also selectivity of the lipase preparation as compared to its selectivity in its free, non-immobilized form or when immobilized on some other supports, is significantly improved.

The lipase/s used in the transesterification/esterification reactions and processes disclosed herein can have varied selectivity towards DHA and EPA, whereby the ratios of EPA:DHA in the form of free fatty acids and fatty acyl groups in fatty acid alkyl esters and glycerides (mono-, di- and tri-glycerides) in the final products may be pre-designed. For example, where high concentration of DHA in the final glycerides product desired, *Thermomyces lanuginosa* [TL] lipase is chosen, while for a high content of EPA and DHA in the final glycerides product desired, either *Alcaligenes* sp. lipase (Lipase QLM™) or *Candida antarctica* A lipase [CALA] can be used. Thus, in order to have final consistent glycerides products containing certain pre-determined ratios between EPA and DHA, according to the present disclosure mixtures of glycerides obtained using different enzymatic systems, which contain certain known ratios of EPA:DHA can be used for the final glycerides products, so as to get the specific desired ratio of EPA:DHA in the final glycerides product.

Still further, there are disclosed herein n-3 fatty acid concentrates, wherein the n-3 fatty acids are substantially EPA, DHA and DPA in their glyceride forms, i.e., as fatty acid moieties of mono-, di- and/or triglycerides, wherein the ratios between said different n-3 fatty acids are pre-determined. These concentrates are useful as nutraceutical ingredients in food products and food supplements, or as food additives, or as ingredients in pharmaceutical preparations. Such additives or pharmaceutical compositions can be presented in liquid form, or in dosage unit forms, for example gelatin capsules, containing the n-3 fatty acids-enriched glyceride mixtures.

Glyceride/s mixtures are any mixtures comprising triglycerides, diglycerides and/or monoglycerides. The ratios between the triglycerides, diglycerides and monoglycerides in a glycerides mixture can be pre-designed.

Polyunsaturated fatty acids as accepted, and as used herein, are fatty acids having four or more double bonds in their carbon chain.

The terms omega-3 fatty acids, ω-3 fatty acids, n-3 fatty acids, omega-3 PUFAs, ω-3 PUFAs and n-3 PUFAs are used herein interchangibly.

The terms fatty acyl, or fatty acyl group, or fatty acid residue or fatty acid moiety are used herein interchangibly, and generally refer to a bonded fatty acid moiety, for example bonded to the glycerol backbone of glycerides and/or polar lipids, or as the acid moiety of a fatty acid alkyl ester.

Throughout this disclosure, unless indicated differently, when referring to levels of n-3 fatty acids or fatty acid moieties by percentages, these are weight percent, and express the weight fraction of n-3 fatty acid moieties out of the total weight of fatty acid moieties. Such percentages are indicated as x % or x % w/w or x % w/w interchangibly.

In some embodiments of the n-3 enrichment processes disclosed herein, there is provided a process that comprises reacting an oil comprising from 5% to 60%, for example from 10% to 35% n-3 fatty acids and a short-chain alcohol or alcohol donor, in the presence of water and a biocatalyst, specifically a lipase immobilized on a polymeric resin comprised of hydrophobic and mild hydrophilic domains, as described above (mixed support). As described in more detail below, due to its immobilization, the biocatalyst (lipase) exhibits increased activity towards the transesterification/esterification reactions, which can occur simultaneously or consecutively in any order, of saturated fatty acids in particular, and to some extent also of mono-, di- and tri-unsaturated fatty acids, and decreased transesterification/esterification activity towards n-3 fatty acids. When the reaction is stopped, the immobilized lipase preparation is removed followed with evaporation, specifically flash evaporation of the reaction medium to remove water and excess of alcohol, and a fraction of glycerides enriched with n-3 fatty acids is obtained via distillation of the fraction comprising fatty acid alkyl esters and free fatty acids formed in the reaction. Distillation can be, for example, molecular or thin-film distillation. The isolated fraction of glycerides comprises over 60% of n-3 polyunsaturated fatty acids present in the starting oil material. This isolated glyceride fraction enriched with n-3 fatty acids, can optionally be further esterified/interesterfied with n-3 free fatty acids concentrate, or n-3 fatty acid short-chain alkyl esters concentrate in the presence of free or immobilized enzyme possessing transesterification/esterification activity, for example *Candida antarctica* lipase B, to form mainly triglycerides mixture with more than 60% n-3 fatty acids, and water and short-chain alcohol as byproducts, respectively. This fraction of triglycerides further enriched with n-3 fatty acids can be obtained by distilling the formed water/alcohol and residual excess of free fatty acids and/or fatty acids alkyl esters from the reaction mixture. It is to be noted that the removed enzyme is recyclable, and can be re-used over numerous circles of the reaction.

The terms "consecutively" and "sequentially" when referring to enzymatic reactions are used herein interchangibly.

In all aspects and embodiments of processes and reactions of the present disclosure, the immobilized enzyme can be used in either multiple batches or continuously in fixed-bed, packed-bed, fluidized-bed, and stirred-tank reactors.

Without being bound by theory, it is suggested that due to the nature of a mixed polymer resin support, as defined herein, on which the lipase is immobilized in specific aspects and embodiments, which support comprises alternating hydrophobic-hydrophilic domains, as detailed above, the enzyme adapts to a new favorite conformation with a smaller active-site cavity compared to its active site cavity when in free form, or when immobilized on other types of polymer support resins of hydrophobic or hydrophilic characteristics. A smaller active-site cavity can lead to increased transesterification/esterification activity rates of the lipase towards short-chain fatty acids, such as lauric, myristic or palmitic fatty acyl groups and to some extent mono-, di- or tri-unsaturated fatty acids such as oleic, linoleic and linolenic acids, and reduced transesterification/esterification activity towards longer-chain fatty acyl groups, such as DPA, EPA, and DHA in their free fatty acid form or as fatty acyl moieties, as compared to its activity in free form or immobilized on different polymeric resins. The present disclosure can thus provide means for changing selectivity towards various types of fatty acyl groups of a lipase by immobilizing such lipase on a mixed polymeric support as disclosed herein.

In all of the presently disclosed processes and compositions, the final concentration (level) of n-3 fatty acids in the glyceride mixture or glyceride concentrate can also be pre-designed, depending on the starting n-3 fatty acid concentrate and also on the source of enzyme.

In addition, as mentioned, the presently disclosed processes can be adapted so as to yield pre-determined ratios of EPA:DHA in the final concentrates, by using lipases which exhibit different specificities towards EPA and DHA. This feature enables the preparation of "costume-made" EPA/DHA fatty acids concentrates, which can be employed in various blends and mixes for the food and nutraceutical industries, according to the intended use. Generally, the weight ratios of EPA:DHA moieties in the concentrates produced in accordance with the present disclosure can range from about 0.01:2 to 5:1 and any sub-values therebetween.

As used herein, the term "about" is meant to encompass deviation of +10% from the specifically mentioned value of a parameter, such as temperature, pressure, concentration, yield, concentration, etc.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

As used herein, the singular form "a", "an" and "the" include plural references unless the context clearly dictates otherwise. For example, the term "a compound of formula (I)" may independently include a plurality of compounds of formula (I), including mixtures thereof.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The following examples are representatives of techniques employed by the inventors in carrying out aspects of the present invention, in a non-limiting manner. It should be appreciated that while these techniques are illustrative of specific embodiments for the practice of the disclosed processes and compositions, those of skill in the art, in light of the present disclosure, will recognize that numerous modifications can be made without departing from the intended scope of the invention.

EXAMPLES

Example 1

Preparation of Immobilized Lipases

Lipases in this work were used in either free form or immobilized on different supports, including microporous silica, polymeric adsorbents of various extents of hydrophilic and hydrophobic characteristics, and on ion exchange resins. Below is a list of the supports used for the immobilization of the different lipases tested in this work.

Enzyme immobilization procedure can be as follows:
Lipase (10,000 units of lipase) derived from different suitable sources as specified, was dissolved in phosphate buffer solution (10 ml) of 0.1M and pH 7. Enzyme support (2 g) in beads form, with particle size distribution in the range of 100-1500 micron, or powderous form (less than 100 micron) was introduced into the enzyme solution. The mixture was shaken for 4-12 hours at room temperature. The enzyme immobilized on the support was filtered off from the solution. Optionally, the filtered enzyme was washed with cold acetone and then dried in a desiccator or a lyophilizer to water content of the immobilized enzyme preparation below 5%.

The lipases used in this work were lipases derived from different sources: *Candida antarctica* A (CALA) and B (CALB), *Rhizomucor miehei, Pseudomonas* sp., *Rhizopus niveus, Mucor javanicus, Rhizopus oryzae, Aspergillus niger, Penicillium camembertii, Alcaligenes* sp., *Burkholderia* sp., and *Thermomyces lanuginosa*.

As an example, CALA was immobilized on the various supports listed below, which possess different hydrophobic-hydrophilic characteristics to form the immobilized lipase preparation:
1. Activated carbon with hydrophobic characteristics (Sigma)
2. Cross-linked styrene-divinylbenzene with hydrophobic characteristics (Amberlite® XAD 1600N, Rohm & Haas, or Lewatit® VP OC 1064 MD PH, Lanxess, Germany)
3. Divinylbenzene-cross-linked with methyl methacrylate comprising distinct (alternating) hydrophobic and mild hydrophilic domains
4. Cross-linked phenol formaldehyde polycondensate resins—weak base anion exchanger with hydrophilic characteristics (Duolite® A568, Rohm & Haas)
5. Methacrylic polymer with hydrophilic characteristics (Amberlite® XAD7HP, Rohm & Haas)
6. Silica gel 60 with hydrophilic characteristics (Sigma-Aldrich, CAS No. 112926-00-8)

Example 2

Preparation of n-3 Fatty Acids Concentrates in the Form of Glycerides

Lipase derived from *Candida antarctica* A (CALA), (15,000 units, NovoCor AD L, Novozymes, Denmark) in its free form or immobilized on each of the six different enzyme supports (Ig) according to Example 1 (designated in the Tables below as "free" or by support number), was contacted with refined fish oil (10 g) (FFAs content below 0.3%, n-3 fatty acids level 30%, EPA 18% and DHA12% w/w) by mixing or shaking, and ethanol (2 g) was added into the reaction system (oil-enzyme mixture) in three equivalent batches each 1 hour apart. The water content in the reaction mixture was adjusted to 3% by weight of oil, by adding the required amount of water or alkaline aqueous buffer solution so that the pH of the reaction medium is in the range of 5-9. The reaction was conducted at 30° C. The reaction products were quantified by gas chromatography at different time intervals. Tables 1, 2 and 3 below show the distribution of the fatty acids ethyl esters in the ethyl esters fraction which were produced in the reaction system at different time intervals.

After 48 hours of stirring the immobilized lipase preparation was filtered off (in this and all of the following examples, where free lipase was used, it precipitated at the end of reaction) and the reaction mixture was flash evaporated to remove excess of water and alcohol, and then was distilled off by fractional molecular distillation (Lab 3™ Centrifugal Distillation System, Myers™, USA) at 10 mTorr and 120° C. to remove fatty acid ethyl esters (FAEEs) and free fatty acids (FFAs) and yield a fraction of fish oil glycerides containing over 60% n-3 fatty acids of the total n-3 fatty acids present in the starting material. The content of n-3 fatty acids in the final glycerides fraction was determined by complete methylation for the mono-, di- and tri-glycerides in the presence of 14% boron trifluoride solution in methanol (product of Sigma-BF3/CH3OH) and analyzing the formed fatty acid methyl esters by gas chromatography.

Table 1 presents the results of transesterification/esterification reaction, conversion of refined fish oil and ethanol to FAEEs, using different preparations of CALA, after 6 hours of reaction.

Reaction Conditions:

Refined fish oil (10 g) containing 3% water and 1 g immobilized lipase preparation (or equivalent lipase units in its crude form) were mixed with ethanol (2 g) which was added into the reaction system (oil-enzyme mixture) in three equivalent batches, each 1 hour apart. The reaction mixture was incubated at 30° C. and shaken at 300 rpm.

TABLE 1

| Enzyme | FAEEs % | EPAEE % | DHAEE % | EPAEE + DHAEE (%) | Omega-3/FAEEs (%) |
|---|---|---|---|---|---|
| Crude CALA | 39.6 | 4.8 | 1.5 | 6.3 | 15.9 |
| CALA/1 | 4.7 | 0.3 | 0.2 | 0.5 | 10.3 |
| CALA/2 | 47.9 | 2.6 | 1.5 | 4.2 | 8.7 |
| CALA/3 | 49.9 | 2.3 | 1.3 | 3.6 | 7.3 |
| CALA/4 | 36.4 | 2.0 | 1.0 | 3.0 | 8.3 |
| CALA/5 | 24.0 | 2.5 | 1.3 | 3.8 | 15.8 |
| CALA/6 | 0.1 | 0.0 | 0.0 | 0.0 | 0.0 |

Table 2 presents the results of transesterification/esterification reaction, conversion of refined fish oil and ethanol using different preparations of CALA to FAEEs after 24 hours of reaction. Reaction conditions were the same as for Table 1.

TABLE 2

| Enzyme | FAEEs % | EPAEE % | DHAEE % | EPAEE + DHAEE (%) | Omega-3/FAEEs (%) |
|---|---|---|---|---|---|
| Crude-CALA | 54.7 | 6.3 | 2.5 | 8.8 | 16.0 |
| CALA/1 | 12.5 | 0.8 | 0.4 | 1.2 | 9.4 |
| CALA/2 | 53.0 | 4.9 | 2.7 | 7.5 | 14.2 |
| CALA/3 | 55.0 | 3.7 | 1.9 | 5.6 | 10.2 |
| CALA/4 | 48.6 | 3.4 | 1.9 | 5.3 | 10.9 |
| CALA/5 | 48.9 | 6.5 | 3.4 | 9.9 | 20.2 |
| CALA/6 | 0.1 | 0.0 | 0.0 | 0.0 | 0 |

Table 3: presents the results of transesterification/esterification reaction, conversion of refined fish oil and ethanol using different preparations of CALA to FAEEs after 30 hours of reaction. Reaction conditions were the same as for Table 1.

TABLE 3

| Enzyme | FAEEs % | EPAEE % | DHAEE % | EPAEE + DHAEE (%) | Omega-3/FAEEs (%) |
|---|---|---|---|---|---|
| Crude-CALA | 64.69 | 10.83 | 3.30 | 14.13 | 21.84 |
| CALA/1 | 11.03 | 0.92 | 0.39 | 1.31 | 11.88 |
| CALA/2 | 66.75 | 5.94 | 2.75 | 8.69 | 13.02 |
| CALA/3 | 63.54 | 4.77 | 2.29 | 7.06 | 11.11 |
| CALA/4 | 60.07 | 4.37 | 2.33 | 6.70 | 11.15 |
| CALA/5 | 50.12 | 6.50 | 3.54 | 10.04 | 20.03 |
| CALA/6 | 0.10 | 0.00 | 0.00 | 0.00 | 0 |

Tables 1 to 3 show clearly that CALA immobilized on a polymeric resin comprised of mild hydrophobic and mild hydrophilic domains (lipase preparation No. 3) has increased its preference towards saturated and mono-, di-, and tri-unsaturated fatty acyl groups and decreased its preference towards n-3 fatty acyl groups as compared to the activity of the same lipase in its free form or when immobilized on other different supports. As seen, for example, in Table 1, while after 6 hours of allowing the reaction to proceed, when using lipase preparation No. 3, the fraction of FAEEs increased to 49.9%, compared to 39.6% with the crude (non-immobilized) CALA, the level of n-3 fatty acid moieties in the FAEEs fraction was 7.3% w/w, compared to 15.9% w/w when using the crude CALA, showing that the major part of the n-3 fatty acids was retained in the glycerides fraction, yielding oil highly enriched with n-3 fatty acid moieties.

Example 3

Preparation of n-3 Fatty Acids Concentrates in the Form of Glycerides

Lipase derived from *Alcaligenes* sp. (10,000 units, lipase QLM™, Meito Sangyo, Japan) in its free form or immobilized on the different enzyme supports (1 g) as in Example 1, the various enzyme preparations were each contacted by mixing or shaking with refined fish oil of FFAs content below 0.3% (10 g) containing 30% n-3 fatty acids, and ethanol (2 g) was added into the reaction system (oil with enzyme) in three equivalent batches each 1 hour apart. The water content in the reaction mixture was adjusted to 2% by weight of oil by adding the required amount of water or alkaline aqueous buffer solution so that the pH of the reaction medium is in the range of 5-9. The reaction was conducted at 30° C. The reaction products were quantified by gas chromatography at different time intervals.

After 6 hours of stirring the immobilized lipase preparation was filtered off and the reaction mixture was flash evaporated to remove excess of alcohol and water, and then was distilled off by fractional molecular distillation to remove fatty acid ethyl esters and free fatty acids and yield a fraction of fish oil glycerides containing n-3 fatty acids with more than 60% recovery yield for the total n-3 fatty acids present in the starting material. Table 4 below shows the conversion of fish oil glycerides to fatty acid ethyl esters and also the n-3 content in the ethyl esters fraction after 6 hours of reaction.

TABLE 4

| Enzyme | FAEEs % | EPAEE % | DHAEE % | EPAEE + DHAEE (%) | Omega-3/FAEEs (%) |
|---|---|---|---|---|---|
| QLM - Crude | 72.5 | 7.1 | 5.5 | 12.7 | 17.5 |
| QLM/1 | 9.6 | 1.0 | 0.4 | 1.4 | 15.0 |
| QLM/2 | 56.7 | 5.1 | 4.9 | 10.0 | 17.5 |

TABLE 4-continued

| Enzyme | FAEEs % | EPAEE % | DHAEE % | EPAEE + DHAEE (%) | Omega-3/FAEEs (%) |
|---|---|---|---|---|---|
| QLM/3 | 61.7 | 3.1 | 6.1 | 9.1 | 14.8 |
| QLM/4 | 10.1 | 0.8 | 0.6 | 1.3 | 13.1 |
| QLM/5 | 69.4 | 7.0 | 5.5 | 12.5 | 18.0 |
| QLM/6 | 59.3 | 3.2 | 6.5 | 9.7 | 16.4 |

The results presented in Table 4 show similar trend as presented in Tables 1-3, in that lipases immobilized on a polymer support comprising hydrophilic-hydrophobic domains exhibit decreased preference towards omega-3 fatty acid groups in the transesterification/esterification reaction system. The low ratio of Omega-3/FAEEs for Lipase QLM/4 is disregarded, as the conversion rate after 6 hours of reaction was relatively low.

Example 4

Preparation of n-3 Fatty Acids Concentrates in the Form of Glycerides

Lipases derived from *Thermomyces lanuginose* (Lipozyme TL 100L, Novozymes, Denmark), *Alcaligenes* sp. (Lipase QLM™, Mieto Sangyo, Japan) and *Pseudomonas* [Lipase PS, Amano Enzymes, Japan] were separately immobilized on polymeric support comprised of divinylbenzene (DVB), and methyl methacrylate (MMA) (at a ratio of 10:1 wt %, respectively) according to Example 1. The lipase preparations were contacted with a mixture of crude fish oil of FFAs content of 24% (10 g) containing 30% n-3 fatty acids by mixing or shaking, and ethanol (2 g), which was added into the reaction system in three equivalent batches each 1 hour apart. The water content in the reaction mixture was adjusted to 3% by weight of oil by adding the required amount of water or an alkaline solution so that the pH of the reaction medium is in the range from 5 to about 9. The reaction was conducted at 30° C. The reaction products and the FFAs values were quantified by gas chromatography at different time intervals.

Tables 5 to 7 below show the transesterification/esterification and hydrolysis profile of fish oil glycerides and FFAs to fatty acid ethyl esters using the different enzyme preparations.

Table 5 presents the transesterification/esterification and hydrolysis profile of fish oil glycerides and FFAs to FAEEs using *Thermomyces lanuginose* lipase immobilized on DVB/MMA polymer resin.

TABLE 5

| Time (h) | FFAs (%) | FAEEs (%) | MAGs (%) | DAGs (%) | TAGs (%) |
|---|---|---|---|---|---|
| 0 | 23.8 | 0.0 | 2.1 | 2.7 | 71.3 |
| 2 | 12.3 | 53.6 | 9.2 | 18.1 | 6.8 |
| 6 | 5.6 | 71.2 | 12.7 | 9.8 | 0.6 |
| 24 | 3.9 | 84.6 | 6.7 | 4.7 | 0.0 |

MAGs = monoacylglycerides
DAGs = diacylglycerides
TAGs = triacylglycerides

Table 6 presents the transesterification/esterification and hydrolysis profile of fish oil glycerides and FFAs to FAEEs using *Pseudomonas* sp. lipase immobilized on DVB/MMA polymer resin. Reaction conditions were as described above.

TABLE 6

| Time (h) | FFAs (%) | FAEEs (%) | MAGs (%) | DAGs (%) | TAGs (%) |
|---|---|---|---|---|---|
| 0 | 23.8 | 0.0 | 2.1 | 2.7 | 71.3 |
| 2 | 14.6 | 50.9 | 8.8 | 18.3 | 7.4 |
| 6 | 7.3 | 74.9 | 9.9 | 6.5 | 1.4 |
| 24 | 3.9 | 89.3 | 5.2 | 1.6 | 0 |

Table 7 presents the transesterification/esterification and hydrolysis profile of fish oil glycerides and FFAs to FAEEs using *Alcaligenes* sp. lipase immobilized on DVB/MMA polymer resin. Reaction conditions were as described above.

TABLE 7

| Time (h) | FFAs (%) | FAEEs (%) | MAGs (%) | DAGs (%) | TAGs (%) |
|---|---|---|---|---|---|
| 0 | 23.8 | 0.0 | 2.1 | 2.7 | 71.3 |
| 2 | 34.2 | 12.2 | 6.1 | 27.1 | 20.4 |
| 6 | 19.1 | 42.7 | 10.0 | 23.4 | 4.8 |
| 24 | 9.5 | 68.7 | 11.5 | 10.3 | 0 |

The results presented in Tables 5 to 7 show that the immobilized lipases catalyze simultaneously or sequentially the transesterification/esterification and hydrolysis reactions of oil glycerides and free fatty acids to yield after 24 hour of reaction mainly fatty acid ethyl esters and low FFAs value, typically lower than 10%.

Example 5

Lipases Immobilized on a Co-Polymer Comprising Hydrophobic Domains and Mild Hydrophilic Domains Polymer and co-polymer supports used in this study were synthesized according to the method reported by Wang and Yang (Wang, Y. and Yang, W., 2004, Langmuir, Vol 20, p. 6225-6231). Different supports with various ratios of divinylbenzene and methyl methacrylate have been synthesized, washed with distilled water and freeze-dried to remove water and residual organic solvents. The enzyme immobilization procedure described in Example 1 was used for the preparation of different lipases on various support compositions. The final products, immobilized lipase preparations, were opaque powderous substances of particle diameter less than 50 micron. Lewatit OC 1600 (LanXess, Germany) grinded to particle size of less than 50 micron was used as a control resin support comprising DVB and MMA as specified by the manufacturer.

Figure 1:
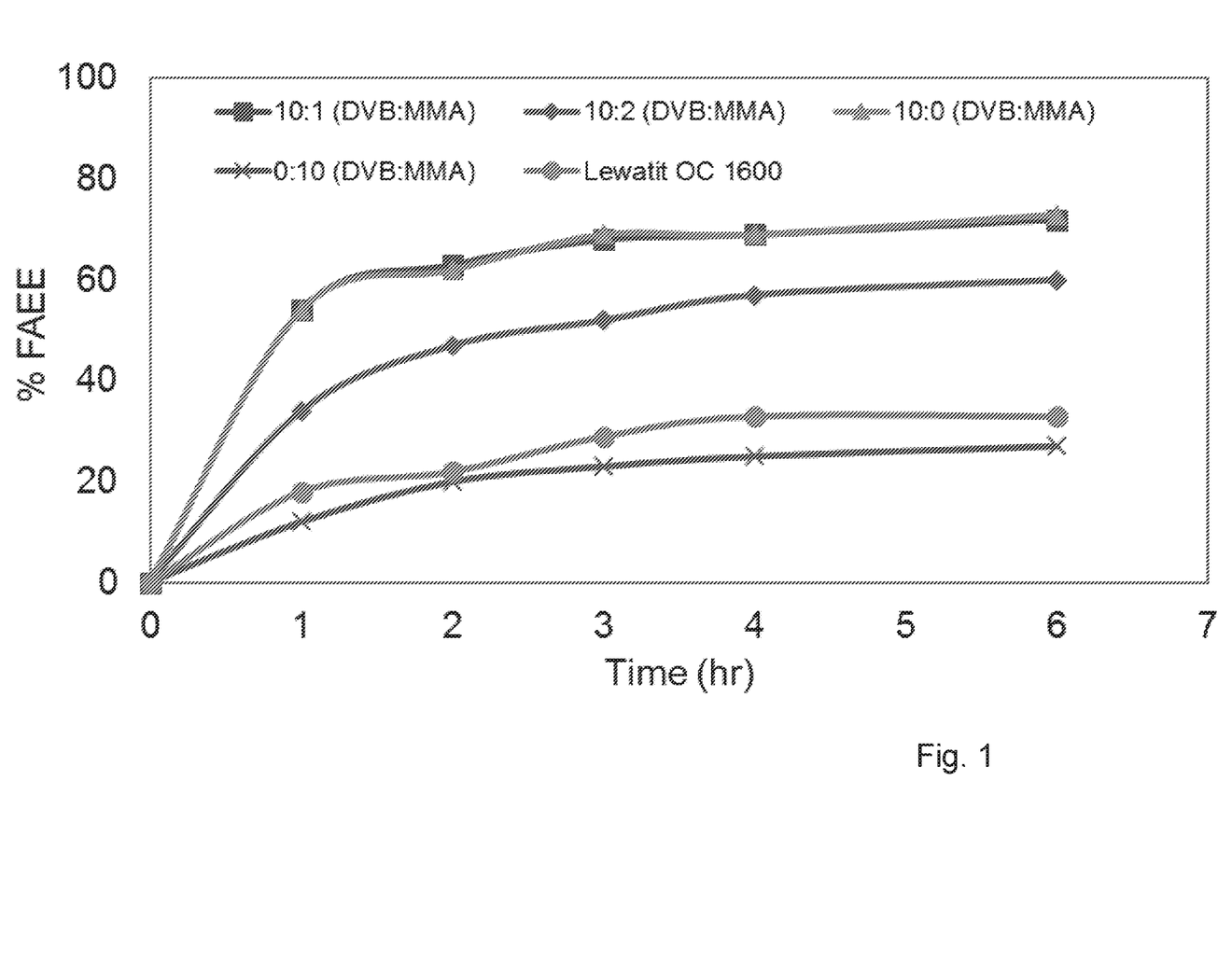
FIG. 1 illustrates the catalytic activity profile of an immobilized *Thermomyces lanuginosa* lipase (Lipozyme TL 100L, Novozymes, Denmark) preparation, wherein the lipase is immobilized on different polymeric resins, each comprising divinylbenzene (DVB) and methyl methacrylate (MMA) at various ratios, in transesterification of refined fish oil and ethanol, in the $4^{th}$ reaction cycle, using the same batch of the immobilized lipase preparation repeatedly. The lipase preparations were used in powderous form. Reaction conditions are detailed in Table 1.

FIG. 1 shows the catalytic activity profile of *Thermomyces lanuginosa* lipase (Lipozyme TL 100L, Novozymes) immobilized on different resins of various ratios of DVB and MMA in transesterification of refined fish oil and ethanol, in the $4^{th}$ reaction cycle, using the same batch of biocatalyst repeatedly. All lipase preparations were used in their powderous form. For reaction conditions see Table 1.

The results presented in FIG. 1 show that the lipase transesterification activity was improved with increasing the content of the hydrophobic monomers as compared to the content of the mild hydrophilic monomers, in this example being DVB (hydrophobic) and MMA (mild hydrophilic). Highest lipase activity was observed when the ratio between DVB/MMA was 10:1, respectively.

Figure 2:
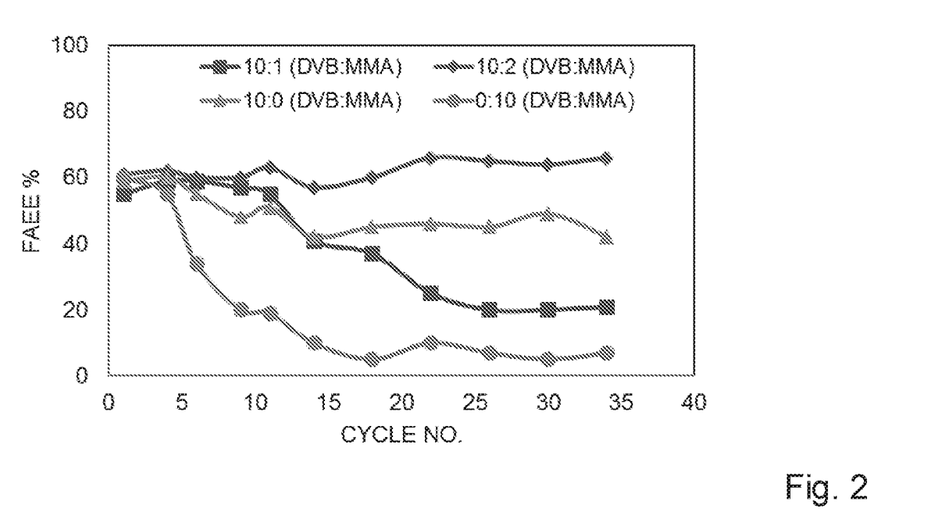
FIG. 2 illustrates the transesterification/esterification conversion rates of refined fish oil and ethanol after 6 hours of reaction using an immobilized *Thermomyces lanuginosa* lipase (Lipozyme TL 100L) preparation, in which the lipase is immobilized on different polymeric resins, each comprising alternating domains of DVB and MMA at various ratios, using the same batch of the immobilized lipase preparation in 35 consecutive reaction cycles. The lipase preparations were used in powderous form. Reaction conditions are detailed in Table 1.

FIG. 2 illustrates the transesterification/esterification conversion rates of refined fish oil and ethanol after 6 hour of reaction using *Thermomyces lanuginosa* lipase (Lipozyme TL 100L) immobilized on different polymer supports comprised of DVB/MMA at different ratios using the same batch of immobilized enzyme beads repeatedly in 35 consecutive reaction cycles. For reaction conditions see example 1.

Figure 3:
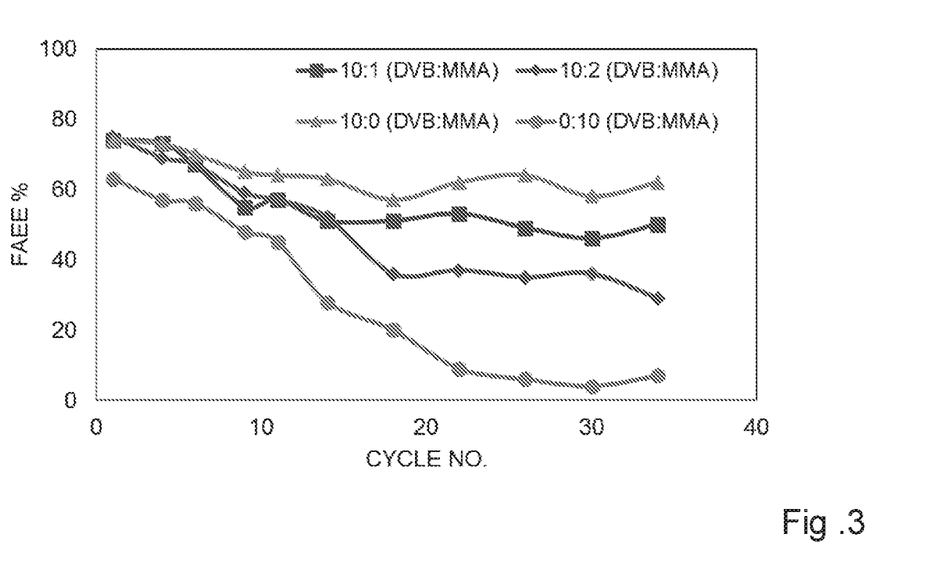
FIG. 3 illustrates the transesterification/esterification conversion rates of refined fish oil and ethanol using an immobilized *Pseudomonas* sp. lipase (Lipase PS Amano) preparation, in which the lipase is immobilized on different polymeric resins, each comprising alternating domains of DVB and MMA at various ratios, using the same batch of the immobilized lipase preparation in 35 consecutive reaction cycles. The lipase preparations were used in powderous form. Reaction conditions are detailed in Table 1.

FIG. 3 illustrates the transesterification/esterification conversion rates of refined fish oil and ethanol using *Pseudomonas* sp. lipase (Lipase PS Amano) immobilized on different polymer supports comprised of DVB/MMA in different ratios using the same batch of immobilized enzyme beads repeatedly in 35 consecutive reaction cycles.

Example 6

Preparation of Fatty Acid Ethyl Esters of Fish Oil by Use of *Pseudomonas* sp. Lipase and Subsequently with *Thermomyces lanuginosa* Lipase Both Immobilized on DVB-MMA Mixed Polymer Support for Non-Selective Transesterification/Esterification of Fish Oil Different preparations of lipases known in the prior art for their low selectivity towards omega-3 fatty acyl groups in the transesterification reaction of fish oil and ethanol, were used in this work in their immobilized form, different preparations containing different amount of enzyme per unit weight of polymer support. The Tables below show the composition of the transesterification reaction medium after 6 and 24 hours of reaction with *Pseudomonas* sp. lipase (Lipase PS Amano), *Alcaligenes* sp. lipase (Lipase QLM™, Meito Sangyo) and *Thermomyces lanuginosa* lipase (Lipozyme TL 100L) at different concentrations of enzymes which were separately immobilized on hydrophobic-mild hydrophilic sequenced polymer support.

Tables 8 and 9 present the composition of the FAEEs % produced after 6 and 24 hours of transesterification reaction of refined fish oil and ethanol using *Pseudomonas* sp. lipase (lipase PS Amano) immobilized on DVB-MMA polymer support with different load of enzyme protein (units enzyme/1 g polymer support).

TABLE 8

| | 6 HR % Components | | | |
|---|---|---|---|---|
| Lipase Preparation | FAEE % | EPAEE % | DHAEE % | EPAEE + DHAEE % |
| PS/Imm. (750 u/g) | 28.00 | 1.60 | 1.80 | 3.40 |
| PS/Imm (2240 u/g) | 55.7 | 4.6 | 5 | 9.60 |
| PS/Imm. (22400 u/g) | 82.6 | 12 | 10.8 | 22.80 |

TABLE 9

| | 24 HR % Components | | | |
|---|---|---|---|---|
| Lipase Preparation | FAEE % | EPAEE % | DHAEE % | EPAEE + DHAEE % |
| PS/Imm. (750 u/g) | 35.50 | 1.90 | 2.80 | 4.70 |
| PS/Imm (2240 u/g) | 63.4 | 6.4 | 7.9 | 14.30 |
| PS/Imm. (22400 u/g) | 94.4 | 18 | 12.5 | 30.50 |

Tables 10 and 11 present the composition of the FAEEs % produced after 6 and 24 hours of transesterification reaction of refined fish oil and ethanol using *Alcaligenses* sp. lipase (lipase QLM Amano) immobilized on DVB-MMA polymer support with different load of enzyme protein (unit enzyme/1 g polymer support).

TABLE 10

| | 6 HR % Components | | | |
|---|---|---|---|---|
| Lipase Preparation | FAEE % | EPAEE % | DHAEE % | EPAEE + DHAEE % |
| QLM/Imm. (2000 u/g) | 42.61 | 2.617 | 2.742 | 5.36 |
| QLM/Imm. (5000 u/g) | 49.96 | 3.081 | 3.703 | 6.78 |
| QLM/Imm. (10000 u/g) | 52.78 | 2.991 | 4.308 | 7.30 |
| QLM/Imm. (20000 u/g) | 55.50 | 3.484 | 4.721 | 8.21 |

TABLE 11

| | 24 HR % Components | | | |
|---|---|---|---|---|
| Lipase Preparation | FAEE % | EPAEE % | DHAEE % | EPAEE + DHAEE % |
| QLM/Imm. (2000 u/g) | 47.80 | 2.60 | 3.20 | 5.80 |
| QLM/Imm. (5000 u/g) | 55.60 | 3.40 | 4.00 | 7.40 |
| QLM/Imm. (10000 u/g) | 60.3 | 3.5 | 4.8 | 8.30 |
| QLM/Imm. (20000 u/g) | 66.2 | 4.6 | 5.5 | 10.10 |

Tables 12 and 13 show the composition of the FAEEs % produced after 6 and 24 hours of transesterification reaction of refined fish oil and ethanol using *Thermomyces lanuginosa* lipase (Lipozyme TL 100L) immobilized on DVB-MMA polymer support with different load of enzyme protein (unit enzyme/1 g polymer support).

TABLE 12

| | 6 HR % Components | | | |
|---|---|---|---|---|
| Lipase Preparation | FAEE % | EPAEE % | DHAEE % | EPAEE + DHAEE % |
| Lipase TL/Imm. (25000 u/g) | 60.66 | 11.919 | 2.752 | 14.67 |
| Lipase TL/Imm. (62500 u/g) | 68.25 | 14.6 | 2.747 | 17.35 |
| Lipase TL/Imm. (125000 u/g) | 69.38 | 14.734 | 2.902 | 17.64 |
| Lipase TL/Imm. (250000 u/g) | 67.35 | 14.35 | 2.768 | 17.12 |
| Lipase TL/Imm. (500000 u/g) | 64.89 | 12.974 | 2.804 | 15.78 |

TABLE 13

| | 24 HR % Components | | | |
|---|---|---|---|---|
| Lipase Preparation | FAEE % | EPAEE % | DHAEE % | EPAEE + DHAEE % |
| Lipase TL/Imm. (25000 u/g) | 72.4 | 14.8 | 3.2 | 18.00 |
| Lipase TL/Imm. (62500 u/g) | 80 | 17.56 | 3.5 | 21.06 |
| Lipase TL/Imm. (125000 u/g) | 79.60 | 17.30 | 3.70 | 21.00 |
| Lipase TL/Imm. (250000 u/g) | 79.00 | 17.40 | 3.30 | 20.70 |
| Lipase TL/Imm. (500000 u/g) | 69.50 | 14.39 | 2.80 | 17.19 |

The results presented in Tables 8 to 13 show that when the concentration of the enzyme protein on the polymer support is increased, *Pseudomonas* sp. lipase transesterified all types of fatty acyl groups, including EPA and DHA acyl groups and reaching approximately 95% conversion after 24 hours of reaction, while *Alcaligenes* lipase (lipase QLM Amano) and *Thermomyces lanuginosa* lipase (Lipase TL) maintained their low selectivity towards omega-3 fatty acyl groups with increasing the enzyme protein load on the polymer support. Importantly, the results show that lipase PS derived from *Pseudomonas* sp. when used at high loads of protein on the polymer support it can be used for the non-selective transesterification/esterification of omega-3 fatty acyl groups-containing oils, to obtain near to complete yields of fatty acid alkyl esters, in particular, fatty acid ethyl esters. Surprisingly, when a two-stage process was conducted, where *Pseudomonas* lipase (Lipase PS, Amano) was used for the transesterification/esterification of fish oil and ethanol reaching a conversion of higher than 70% and then the upper organic phase of the reaction medium was collected by removing the glycerol and water phase from the reaction mixture, and reacted again with ethanol in the presence of *Thermomyces lanuginose* lipase immobilized on divinylbenzene/methyl methacrylate polymer resin a conversion of close to 100% was achieved. The recyclability of both enzymes has also been tested in two-stage enzymatic transesterification process and it was demonstrated that both lipase preparations maintained more than 70% of their initial enzyme activity after at least 20 cycles. These results show that the use of a lipase derived from *Pseudomonas* sp. alone or in combination with other types of lipases characterized with high transesterification/esterification catalytic activity and stability such as *Thermomyces lanuginosa* lipase, would be of high industrial interest for replacing the conventional chemical transesterification of omega-3 oils with an all-enzymatic process, so as to obtain conversion close to 100% of the esterifiable fatty acids to fatty acid ethyl esters. Fractional distillation can be used at the end of the process, after achieving 100% conversion to fatty acid ethyl esters in order to obtain omega-3 fatty acids concentrates typically in the range of 50-70%.

Example 7

Preparation of Polyunsaturated Fatty Acids-Enriched Triglycerides

A mixture containing different ratios of mono-, di- and tri-glycerides obtained as in Examples 2 or 3 (after distilling off the ethyl esters and free fatty acids fractions) was reacted with n-3 fatty acid concentrates of 80% in the form of free fatty acids or in the form of FAEEs using Novozym 435 (Novozymes, Denmark), or CALB immobilized on a suitable polymeric resin. The reaction was conducted at 60° C. under vacuum to remove the formed water or ethanol from the reaction system. After reaching conversion of more than 70% of the partial glycerides that were present in the initial glyceride fraction to triglycerides, the immobilized biocatalyst was filtered off. The product typically comprised more than 70% of the total glycerides of triglycerides containing n-3 polyunsaturated fatty acids at levels of above 60% depending on the starting fatty acids composition.

The invention claimed is:

1. An enzymatic process for the enrichment of n-3 polyunsaturated fatty acids (n-3 PUFA) as glycerides, said process comprising:
(a) providing an oil having n-3 PUFA moieties content of from about 5% to about 60% w/w, the n-3 PUFA moieties be present as free acids or as acyl groups of glycerides and/or polar lipids contained in said oil;
(b) adding to said oil, water or alkaline aqueous buffer solution at an amount of 1-10% w/w of said oil, to give a reaction medium with pH of from about 5 to about 9;
(c) adding to the reaction medium obtained in step (b) a lipase, wherein said lipase is immobilized on a suitable polymeric support, wherein said lipase exhibits high selectivity toward saturated fatty acids, mono-, di- and tri-unsaturated fatty acids or their fatty acyl groups, and is capable of simultaneously or consecutively transesterifying and/or esterifying said oil;
(d) providing an alkyl alcohol or alcohol donor, and adding said alkyl alcohol or alcohol donor to the reaction medium of said oil and said lipase obtained in step (c) to form a reaction system comprising said lipase and a reaction medium comprising said oil, said water or alkaline aqueous buffer solution and said alcohol, wherein said oil reacts with said alcohol, and allowing said reaction to reach a conversion of at least 40% of said oil to fatty acid alkyl esters (FAEEs), less than 10% free fatty acid (FFAs) and from about 15% to about 60% glycerides by weight of oil used in the reaction system;
(e) stopping the reaction by removing the said reaction medium from said reaction system followed with evaporation to remove excess of alcohol and water to give a product comprising FAEEs, FFAs and a mixture of mono-, di- and tri-glycerides, and optionally polar lipids; and
(f) isolating the said glycerides from said FAEEs and FFAs by distilling off said fatty acid alkyl esters and free fatty acids from the product obtained in step (e) to give a distillate comprising FAEEs and FFAs, and a residue comprising glycerides mixture and optionally polar lipids, wherein said glycerides mixture contains higher omega-3 fatty acids content compared to said oil, with recovery yield of higher than 60%,
wherein said immobilized lipase maintains at least 60% of its catalytic activity over at least 10 reaction cycles using the same batch.

2. The process according to claim 1, wherein said mixture of fatty acid alkyl esters and free fatty acids distilled off the product comprises less than 40% n-3 fatty acid moieties out of the total n-3 fatty acids present in said oil.

3. The process according to claim 1, wherein said alcohol is any one of ethanol or methanol and said alcohol donor is any one of dimethyl or diethyl carbonate.

4. The process according to claim 2, wherein said n-3 fatty acid moieties are any one of docosahexaenoic acid (DHA), docosapentaenoic acid (DPA), and eicosapentaenoic acid (EPA) moieties, and any mixture of at least two thereof.

5. The process according to claim 1, wherein said lipase is derived from any one of *Candida antarctica* A (CALA), *Rhizomucor miehei*, *Pseudomonas* sp., *Rhizopus niveus*, *Mucor javanicus*, *Rhizopus oryzae*, *Candida antarctica* B (CALB), *Aspergillus niger*, *Penicillium camembertii*, *Alcaligenes* sp., *Burkholderia* sp., *Thermomyces lanuginosa* or *Chromobacterium viscosum*.

6. The process according to claim 1, wherein said lipase is immobilized on a hydrophobic porous polymeric resin support.

7. The process according to claim 1, wherein the said glycerides mixture obtained in step (f) is further reacted with at least one of (i) an n-3 FFAs concentrate, or (ii) an n-3 fatty acids short-chain alkyl esters concentrate, in the presence of a suitable lipase in its free form or immobilized on a polymeric resin support in a reaction mixture under vacuum and a temperature of 30-80° C., to give a glycerides mixture with more than 60% triglycerides containing more than 60% n-3 fatty acids after distillation of the excess of fatty acids ethyl esters and/or fatty acids, and alcohol and/or water byproducts from the reaction mixture.

8. The process according to claim 1, wherein said oil is an edible oil.

9. The process according to claim 1, wherein said alcohol or alcohol donor is stepwise added to the mixture of said oil and said immobilized lipase obtained in step (c).

10. The process of claim 1, wherein said lipase is derived from *Candida antarctica* A (CALA), *Pseudomonas* sp., *Alcaligenes* sp. or *Thermomyces lanuginose*.

11. The process of claim 1, wherein said support is a hydrophobic aliphatic or aromatic resin support.

12. The process of claim 1, wherein said support is hydrophobic aromatic resin is cross-linked divinylbenzene (DVB) or styrene or cross-linked styrene-DVB.

13. The process of claim 1, wherein said oil is an edible oil selected from fish or algal oil, fungal oil, or a suitable oleaginous substance containing n-3 fatty acids.

14. The process of claim 1, wherein said suitable polymeric support is a polymeric resin support in which said resin comprises alternating hydrophobic domains and mild hydrophilic domains.

15. The process of claim 1, wherein said suitable polymeric support is a polymeric resin support in which said resin comprises alternating hydrophobic domains and mild hydrophilic domains, said hydrophobic domains comprise of hydrophobic aliphatic or aromatic monomers and said mild hydrophilic domains comprise of acrylic and/or methacrylic esters.

* * * * *